(12) United States Patent
Graf et al.

(10) Patent No.: US 7,749,200 B2
(45) Date of Patent: Jul. 6, 2010

(54) ADMINISTRATION DEVICE COMPRISING A PRIMING FUNCTION

(75) Inventors: Roney Graf, Burgdorf (CH); Fritz Kirchhofer, Sumiswald (CH)

(73) Assignee: TecPharma Licensing AG, Burgdorf (CH)

( * ) Notice: Subject to any disclaimer, the term of this patent is extended or adjusted under 35 U.S.C. 154(b) by 0 days.

(21) Appl. No.: 11/035,030

(22) Filed: Jan. 13, 2005

(65) Prior Publication Data

US 2005/0154351 A1 Jul. 14, 2005

Related U.S. Application Data

(63) Continuation of application No. PCT/CH03/00457, filed on Jul. 8, 2003.

(30) Foreign Application Priority Data

Jul. 17, 2002 (DE) .................... 102 32 412

(51) Int. Cl.
*A61M 5/00* (2006.01)
(52) U.S. Cl. ............... 604/187; 604/209; 604/208; 604/232
(58) Field of Classification Search ......... 604/187, 604/207–211, 218, 188, 232–234, 186, 169, 604/181
See application file for complete search history.

(56) References Cited

U.S. PATENT DOCUMENTS

| 4,865,591 | A | | 9/1989 | Sams |
| 4,936,833 | A | | 6/1990 | Sams |
| 5,295,976 | A | | 3/1994 | Harris |
| 5,545,147 | A | * | 8/1996 | Harris ................. 604/209 |
| 5,643,214 | A | | 7/1997 | Marshall et al. |
| 5,728,074 | A | | 3/1998 | Castellano et al. |
| 5,961,495 | A | * | 10/1999 | Walters et al. ............ 604/208 |
| 6,086,567 | A | | 7/2000 | Kirchhofer et al. |
| 6,146,361 | A | * | 11/2000 | DiBiasi et al. ............ 604/232 |
| 6,228,067 | B1 | | 5/2001 | Gabriel |
| 6,277,101 | B1 | | 8/2001 | Kirchhofer et al. |
| 6,312,413 | B1 | * | 11/2001 | Jensen et al. ............ 604/232 |
| 6,699,224 | B2 | | 3/2004 | Kirchhofer et al. |

(Continued)

FOREIGN PATENT DOCUMENTS

DE 199 00 792 C1 6/2000

(Continued)

*Primary Examiner*—Kevin C Sirmons
*Assistant Examiner*—Phillip Gray
(74) *Attorney, Agent, or Firm*—Dorsey & Whitney LLP; David E. Bruhn, Esq.

(57) ABSTRACT

An administering apparatus for administering a fluid product, including a casing, a reservoir for the product, a driven device which acts on the product contained in the reservoir to deliver the product, and a drive device which acts on the driven device and performs a delivery stroke in a drive direction from a delivery position up to a delivery stopper to deliver a product dosage to be administered, wherein a priming stopper is provided for the drive device and limits a priming stroke of the drive device, which serves to bleed, in the drive direction, wherein the priming stroke is axially shorter than a maximum delivery stroke, and wherein the drive device can be moved in the drive direction from a priming position up to the priming stopper and transversely to the drive direction as far as the delivery position.

35 Claims, 5 Drawing Sheets

U.S. PATENT DOCUMENTS

| | | |
|---|---|---|
| 7,316,670 B2 | 1/2008 | Graf et al. |
| 2001/0020155 A1* | 9/2001 | Mikkelsen et al. .......... 604/187 |
| 2003/0004467 A1 | 1/2003 | Musick et al. |

FOREIGN PATENT DOCUMENTS

| | | |
|---|---|---|
| EP | 0 937 477 A2 | 8/1999 |
| EP | 0 713 403 B1 | 12/1999 |
| WO | WO 9504563 | 2/1995 |
| WO | WO 9736625 | 10/1997 |
| WO | WO 02/30495 A2 | 4/2002 |

* cited by examiner

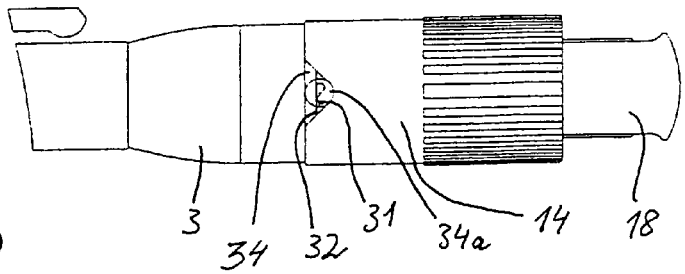
Fig. 9
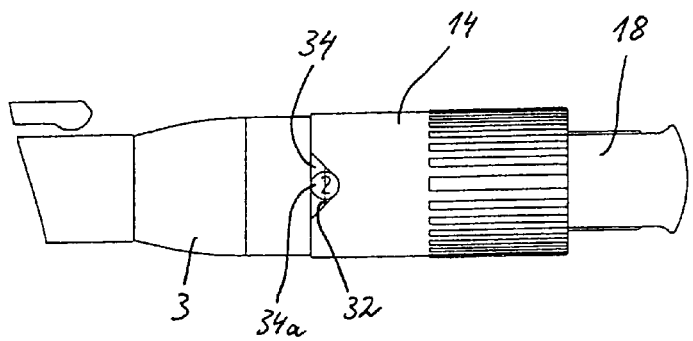
Fig. 10
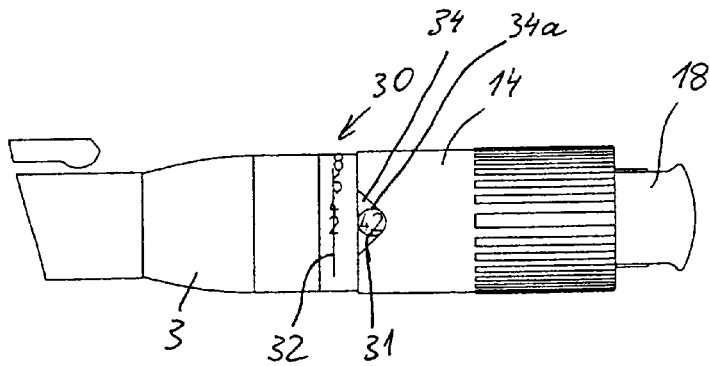
Fig. 11
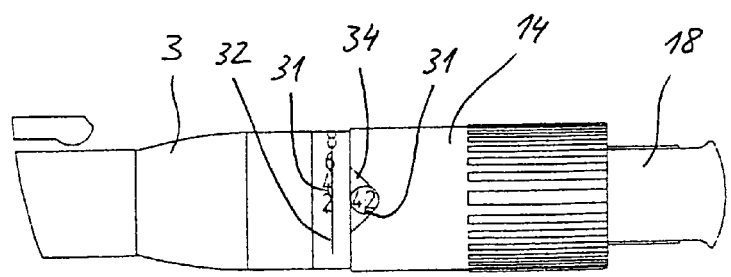
Fig. 12
Fig. 13

ADMINISTRATION DEVICE COMPRISING A PRIMING FUNCTION

CROSS REFERENCE TO RELATED APPLICATIONS

This application is a continuation of International Application No. PCT/CH03/00457, filed on Jul. 8, 2003, which claims priority to German Application No. 102 32 412.3, filed on Jul. 17, 2002, the contents of which is incorporated herein by reference.

BACKGROUND

The invention relates to devices and methods for administering substances, including fluid products, for a variety of uses including medical, veterinary, therapeutic, diagnostic, pharmaceutical and/or cosmetic uses. Some preferred examples of administering devices or apparatus comprise injection apparatus, in particular injection pens, and also inhalation apparatus.

In the above-noted uses or applications, it is in most cases important that a very particular product dosage, i.e., a very particular amount of product, is administered. One source of uncertainty in this regard is the possibility that a part of the apparatus which guides the product is not completely filled with the product, but contains air. Without bleeding, the air—or more generally a gas—would be administered together with the product. In the case of subcutaneous administering, for example, while this would not lead to health complications, the correct product dosage would not be administered, but rather a dosage reduced by the air content. In other modes of administering, however, health can additionally be compromised if air is administered together with the product.

Not only can air be present in the product-guiding part of an administering apparatus when product is administered from a reservoir for the first time, but this can also occur, again or for the first time, after administering a prior administration. For instance, a liquid product in an injection cannula can evaporate from the tip of the cannula and dry up the cannula. If, due to the prevailing pressure conditions, a continuing flow of product from the reservoir side is not possible or is not sufficiently rapid, a volume of air forms in the injection cannula from the tip. If product is subsequently administered again, without bleeding beforehand, then the product dosage administered is reduced in accordance with this volume of air.

WO 97/36625, DE 199 00 792 C1 and U.S. Pat. No. 6,228, 067 B1 describe administering apparatus which are injection pens which allow the product dosage to be selected. In order to prime the known apparatus, the user presses product through the injection needle of the respective apparatus according to "instinct", until he has visually confirmed that product is exiting the tip of the needle. Such priming, as bleeding is generally referred to, "by sight" and "instinct" can have the result that an unnecessarily large amount of product is delivered for the purpose of priming and is therefore lost for administering. Moreover, for people with impaired vision, there is an increased risk that the priming process is not correctly performed due to the necessary visual check, which can result in an even greater unnecessary consumption of product or in incomplete bleeding.

In other administering apparatus, for example in inhalation apparatus, it may also be the case—depending on the design—that air cannot be visually monitored in the product-guiding part of the apparatus at all and that it is, therefore, even more difficult to monitor the administering of a particular product dosage.

SUMMARY

It is an object of the present invention to improve administering devices, for example to increase the reliability or assurance that a particular product dosage or dose known to and/or selected by the user is, in fact, administered.

In one embodiment, the present invention comprises an administering apparatus for administering a fluid product, including a casing, a reservoir for the product, a driven device which acts on the product contained in the reservoir to deliver the product, and a drive device which acts on the driven device and performs a delivery stroke in a drive direction from a delivery position up to a delivery stopper to deliver a product dosage to be administered, wherein a priming stopper is provided for the drive device and limits a priming stroke of the drive device, which serves to bleed, in the drive direction, wherein the priming stroke is axially shorter than a maximum delivery stroke, and wherein the drive device can be moved in the drive direction from a priming position up to the priming stopper and transversely to the drive direction as far as the delivery position.

In one embodiment, an administering apparatus for administering a fluid product, such as the invention relates to, comprises a casing with a reservoir for the product, a driven device which acts on the product in order to deliver the product, and a drive device which acts on the driven device. The drive device can be moved in a drive direction from a delivery position up to a delivery stopper. This delivery movement is preferably a linear translational movement, but can in principle also be performed along a curved arc and can also be or comprise a rotational movement. The complete movement of the drive device from the delivery position up to the delivery stopper is also referred to in the following as the delivery stroke. The drive device is coupled to the driven device such that the movement of the drive device towards the delivery stopper operates the driven device and thus delivers product from the reservoir and through a product-guiding system which is preferably connected to the reservoir. The product-guiding system extends from the outlet of the reservoir to an exit point for the product. In the case of an injection apparatus comprising an injection cannula, for example in the form of a hollow injection needle, the injection cannula generally forms the entire product-guiding system downstream of the reservoir.

The reservoir can be formed by the casing itself. In some preferred embodiments, however, a product container accommodated by the casing, for example in the casing, forms the reservoir. The product container can be an ampoule pre-filled with product.

In accordance with the invention, a priming stopper is provided for the drive device and limits a priming stroke of the drive device, which serves to bleed, in the drive direction, such that the priming stroke is shorter in the drive direction than a maximum delivery stroke. The drive device can not only assume the delivery position but also a priming position from which it can be moved in the drive direction up to the priming stopper and transversely to the drive direction as far as the delivery position. The movement from the priming position to the delivery position can be at right angles to the drive direction or can be at a different angle; in this respect, it need only be stated that said movement has a transverse component with respect to the drive direction. However, a movement running exactly at right angles to the drive direction does represent a preferred embodiment. Since the drive device can not only perform the delivery stroke serving to administer the product but also the priming stroke having a defined length, it is possible to reliably bleed the fluid-guiding system without a visual check. Due to the defined length of the priming stroke, the user also knows what amount of product he has maximally "lost" through the priming process. This is particularly beneficial for people with impaired vision.

The priming stroke preferably occurs between two stopper positions, fixed as viewed in the drive direction, one of which is the priming position and the other of which is defined by the priming stopper. However, it is not to be ruled out that the priming stopper or a stopper defining the priming position can be adjusted, in order to be able to adapt the length of the priming stroke to specific requirements within certain limits. The priming stroke is on the one hand shorter than the delivery stroke, but on the other hand long enough to reliably ensure that the product-guiding parts of the administering apparatus from the reservoir up to the nearest exit point downstream of the reservoir are bled in all operational conditions. The maximum delivery stroke in an apparatus which permits the dosage to be selected corresponds to the maximum selectable dosage. In apparatus in which the option of selecting the dosage is not provided, the maximum delivery stroke is likewise to be designated as the length of the stroke which delivers the maximum product dosage which can be delivered in one stroke using the apparatus in question. This category includes not only apparatus in which the entire reservoir is emptied in a single stroke but also apparatus whose reservoir is emptied in a number of delivery strokes of invariable length. In this case, each of the delivery strokes is a maximum delivery stroke.

In some preferred embodiments, the priming stroke is approximately at least ten to at least twenty times, more preferably at least twenty times, shorter than the maximum delivery stroke. If a dosage unit represents the smallest product dosage which can be administered, and the product dosage can only be administered in whole multiples of the dosage unit, then the minimum priming stroke corresponds to one dosage unit. More preferably, it corresponds to a few dosage units, for example two or three dosage units.

In a preferred embodiment, the drive device can not only be moved from the priming position to the delivery position but also from the delivery position to the priming position. The drive device can be selectively moved from one position to the other. In a disposable apparatus whose reservoir is emptied in a single delivery stroke, however, it is sufficient if the drive device can only be moved once from the priming position to the delivery position and not back again from the delivery position to the priming position. Preferably, the drive device can be moved from the priming position directly to the delivery position, i.e., without a stroke movement in the drive direction. In principle, however, it would also be conceivable for the priming stroke to be performed from the priming position in a first step and, only once it has then reached the stopper position, for the drive device to be moved to the delivery position by a transverse movement. The option of transferring from the priming position to the delivery position without an intermediate stroke movement in the drive direction is, however, particularly advantageous when the drive device can be moved back and forth between the priming position and the delivery position within the context of a selecting movement. The drive device preferably assumes the same height with respect to the drive direction in its delivery position and in its priming position, such that a selecting movement can advantageously be a simple movement at right angles to the drive direction.

In a preferred embodiment, the administering apparatus allows the product dosage to be administered to be selected by the user. It therefore comprises a dosing member which forms a dosing stopper and is coupled to the casing such that it can perform a dosing movement relative to the casing. The dosing stopper is adjusted relative to the drive device by the dosing movement. The dosing stopper lies opposite the delivery stopper, preferably axially, counter to the drive direction. The distance between the dosing stopper and the delivery stopper, measured in the drive direction, corresponds to the delivery stroke of the drive device.

For performing the dosing movement, the dosing member is preferably coupled only to the casing. The coupling can comprise a swivel joint or can be formed by a swivel joint alone. Thus, the dosing member can, for example, be connected to the casing such that it can only be rotated about a fixed rotational axis and can comprise a stepped or continuously spiral dosing stopper such as is described in WO 97/36625 and DE 199 00 792 C1. The swivel joint is more preferably formed by a direct threaded engagement between the casing and the dosing member, i.e., takes the form of a screw joint. For performing the dosing movement, the dosing member can also, however, alternatively be coupled to the drive device on the one hand and the casing on the other, each preferably in direct engagement. In principle, it is also conceivable that the dosing member for the dosing movement is only coupled to the drive device and not to the casing, but is merely mounted by the casing such that it can perform its dosing movement.

In a preferred embodiment, the dosing stopper is formed in such a way that drive device can be moved counter to the drive direction, i.e., away from the delivery stopper, up to the dosing stopper and can be moved in the drive direction up to the delivery stopper. The dosing movement of the dosing member can be a purely axial translational movement or a purely rotational movement with the axial line as the rotational axis. Preferably, the dosing movement of the dosing member is an axial translational movement in combination with a rotational movement about the axial line, such as is, for example, generated by the screw joint cited.

It is particularly advantageous if the dosing movement of the dosing member is or comprises an axial translational movement, since this enables the dosing stopper to assume a single height in the axial direction.

In some preferred embodiments, the priming stopper is formed by the dosing member. Alternatively, the casing can form the priming stopper, or also another intermediate body of a priming mechanism, for example if the administering apparatus does not include a dosing member.

In the preferred embodiment in which the priming function is fulfilled by a direct engagement between the drive device and the dosing member, such a priming mechanism comprises the dosing member and the drive device only. In the alternative embodiment in which the priming function is fulfilled by an engagement between the drive device and the casing, the casing and the drive device only form the priming mechanism. In principle, however, it is also conceivable for the priming mechanism to comprise another body which engages with either the dosing member or the casing on the one hand, and with the drive device on the other, in order to fulfil the priming function. Lastly, it may also be mentioned that it is in principle also possible to incorporate a number of other bodies into such a priming mechanism. Simply coupling by directly engaging the drive device with either the dosing member or the casing is, however, a preferred embodiment.

For fulfilling the priming function, coupling the drive device to the casing instead of to a dosing member is advantageous when the dosing member comprises a stepped dosing stopper or a spiral, continuous dosing stopper, such as is known from WO 97/36625 and DE 199 00 792 C1. When the dosing member is formed in this way, the movement of the drive device from the priming position to the delivery position can firstly comprise the priming stroke, then a movement along the delivery stopper and finally the movement against the dosing stopper. The delivery stopper would simultaneously form the priming stopper. Forming the priming mechanism in this way can also be realized in connection with the dosing member which can be moved axially. In this embodiment, however, forming the priming mechanism by engaging the drive device and the dosing member is advantageous not least because the priming stroke can be performed from a position of the drive device in which the drive device abuts the dosing stopper.

In some embodiments, the possible movements of the drive device are predetermined by a guiding link which comprises a guiding curve and an engaging member which engages with said guiding curve, or consists of these two joint elements only. In a preferred embodiment, the guiding curve is formed by two guiding sections, separate from each other and each extending in the drive direction, with which the engaging member selectively engages. The longer of the guiding sections defines the delivery stroke. The shorter of the guiding sections defines the priming stroke. In order to be able to transfer the engaging member from the one guiding section to the other, the guiding curve further comprises a connecting section. If the guiding curve and the engaging member are formed on mutually facing surface areas of, for example, the dosing member and the drive device, the connecting section can be formed by a cavity on the surface area which forms the guiding curve. In such an embodiment, however, the connecting section can also quite simply be formed a free facing end of the body which forms the guiding curve.

In preferred embodiments, the driven device comprises a piston which can be axially moved in the reservoir in an advancing direction towards an outlet of the reservoir, in order to force product out of the reservoir. Ampoules which are provided pre-filled by the manufacturers are usually already sealed at their rear end by means of such a piston. If a piston is used, the delivery movement of the drive device is preferably an axial, linear movement.

If the product is conveyed by a piston, then the driven device further comprises a piston rod which acts directly on the piston, in order to move it in the advancing direction. Such a piston rod can be formed integrally with the piston or produced separately from the piston and connected, axially rigid, to the piston in a positive, non-positive or frictional lock. In some preferred embodiments, the piston and the piston rod are separate parts, and the piston rod presses in the advancing direction against a rear side of the piston.

In preferred embodiments, the piston rod is mounted by the casing such that it can be moved in the advancing direction but not counter to the advancing direction. In this case, movement counter to the advancing direction is at most possible by appropriate assembling hand operations in the course of exchanging a reservoir. In some preferred embodiments, however, it is not possible to restore the piston rod. Rather, the administering apparatus is completely replaced with a new one. It would also be conceivable to divide the apparatus into a reservoir module designed as a disposable module, and a dosing and drive module which can be repeatedly used with new reservoir modules. This design has already been successfully pursued for injection apparatus in the form of so-called semi-disposable injection pens and can also be advantageously used for the administering apparatus of the present invention.

The fluid product is preferably a liquid for medical, therapeutic, diagnostic, pharmaceutical or cosmetic applications or uses, or for a number of these applications in combination. The product can for example be insulin, a growth hormone, cortisone, collagen or also liquid nutrition. Also, the administering apparatus is used in applications in which a user administers the product himself, as is, for example, usual in diabetes therapy. Use of the apparatus only or also in the ward or for treatment of out-patients by trained personnel is not, however, to be ruled out.

In the case of an injection apparatus, the product can be administered by means of an injection cannula or, for example, a nozzle for needle-free injections. The injection can be subcutaneous or venous, or also intramuscular. The administering apparatus can be an inhalation apparatus in which the selected product dosage or a remaining dosage still present in the reservoir is delivered from the reservoir, for example into a chamber of the inhalation apparatus, and atomised by means of a vaporiser or other atomising means for inhalation. Furthermore, oral ingestion of the product is conceivable, or administering via the esophagus, to name but a few administering examples.

BRIEF DESCRIPTION OF THE DRAWINGS

FIG. 9 depicts a view onto a dosage display in the apparatus state in FIG. 6;

FIG. 10 depicts the view onto the dosage display after a "loading process" from the state in FIG. 9;

FIG. 11 depicts the view onto a dosage display in the apparatus state in FIG. 7;

FIG. 12 depicts the view onto a dosage display in the apparatus state in FIG. 8; and FIG. 13 depicts a dosage scale, unwound onto the plane of the page.

DETAILED DESCRIPTION

Figure 1:
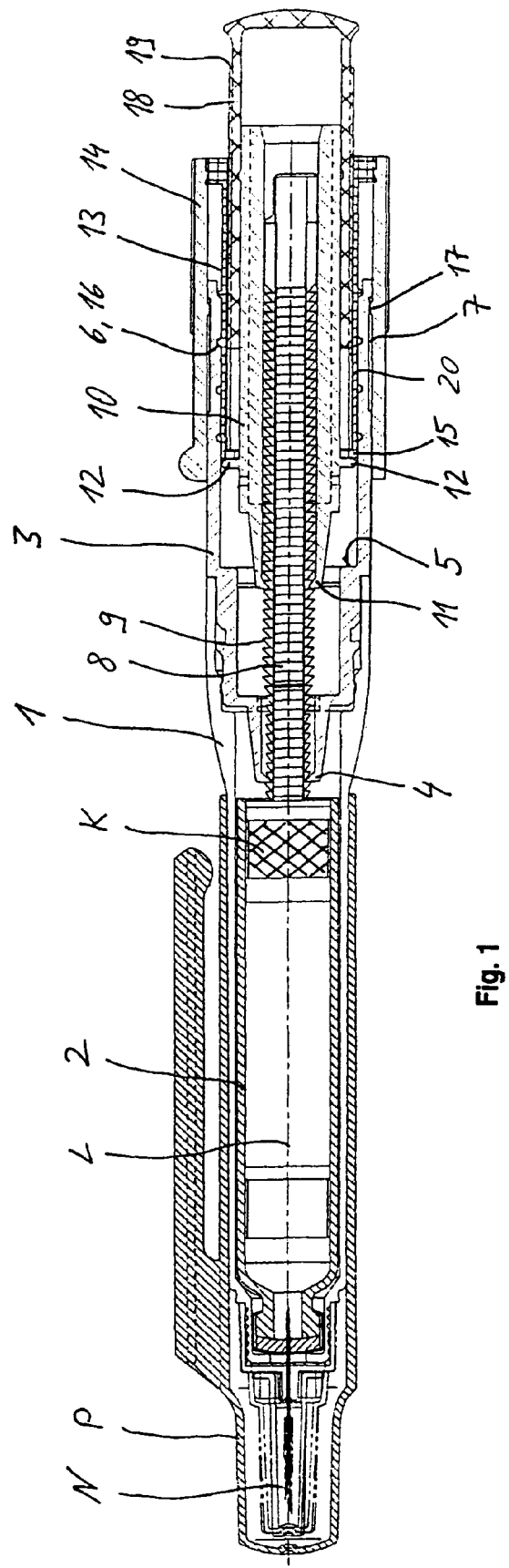
FIG. 1 depicts an injection apparatus in a longitudinal section.

FIG. 1 shows a longitudinal section of one embodiment of an administration apparatus, namely, and injection apparatus in the form of a gear rack pen for self-administering, for example, insulin or growth hormones. A first, front casing section 1 and a second, rear casing section 3 form a casing of the pen. The casing sections 1 and 3 are sleeve bodies. To form the casing, they are plugged into each other along a common central longitudinal axis L, in a non-releasable connection. Furthermore, the connection is such that the casing sections 1 and 3 cannot be moved relative to each other, either axially or rotationally about the longitudinal axis L.

An ampoule 2 accommodated in the front casing section 1 forms a reservoir for a product which is administered by way of injection using the pen. An outlet of the ampoule 2 is sealed by a membrane. An injection needle N is, however, guided through the membrane and protrudes via a rear end into the ampoule 2. A piston K is accommodated at a rear end of the ampoule 2 facing away from the outlet. An axial movement of the piston K along the longitudinal axis L in an advancing direction pointing towards the ampoule outlet delivers product from the ampoule 2 and through the injection needle N, thus administering it. In the state shown, the front casing section 1 is covered by an outer protective cap P and the injection needle N, still separate, is covered by an inner protective cap which of course has to be removed before administering.

The rear casing section 3 forms a mechanism holder by mounting a piston rod 8 acting on the piston K in the advancing direction and the other components of the pen which participate in selecting a product dosage to be delivered and in delivering the product dosage selected. These other components are a drive member 10 and an operating element 18 which together form a drive device for the piston rod 8, and furthermore a dosing member which, in co-operation with the rear casing section 3, serves to select the product dosage or dose to be delivered from the ampoule 2.

Figure 2:
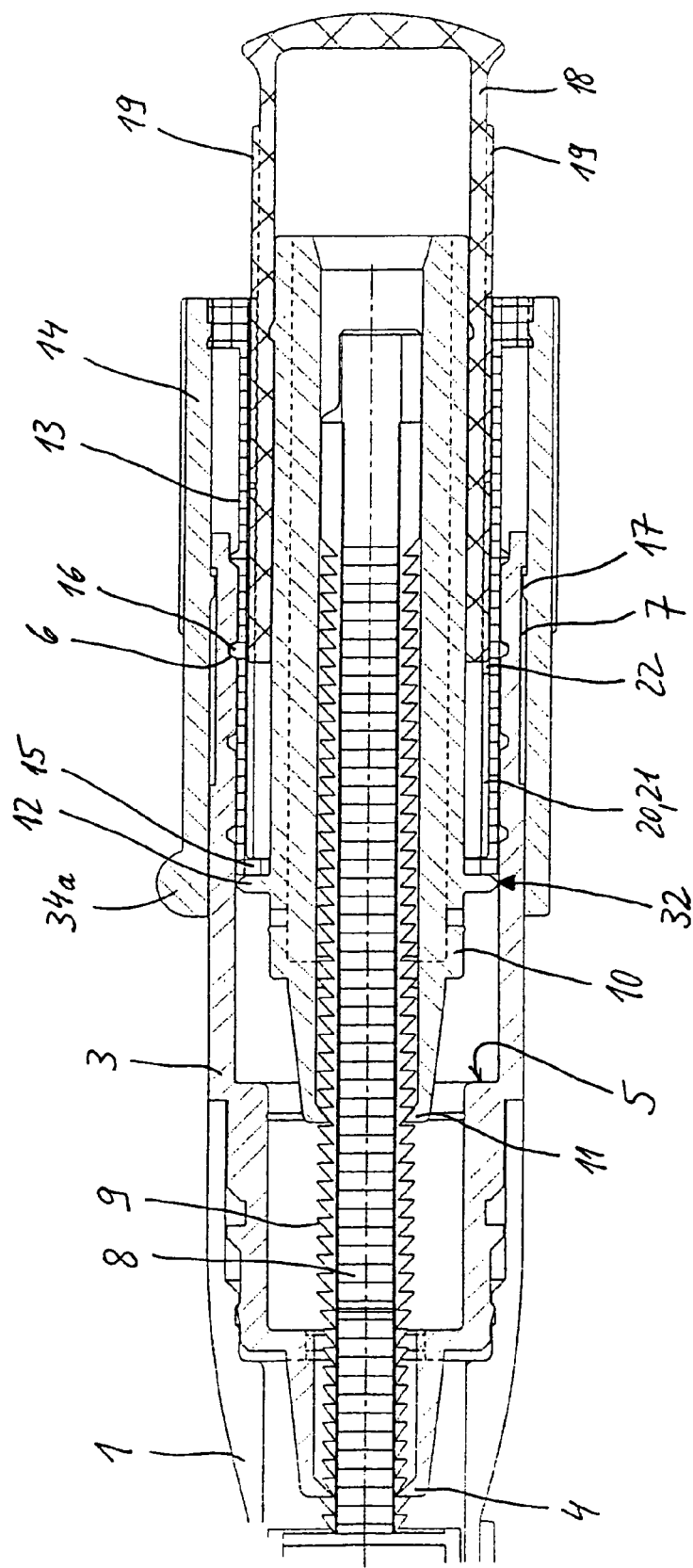
FIG. 2 depicts the rear part of the injection apparatus.

In FIG. 2, these components and their couplings are shown enlarged. Reference may also be additionally made to the cross-sectional representation in FIG. 3.

On the outer surface of the piston rod 8, four rows of teeth 9 formed from serrated teeth extend in the longitudinal direction, respectively offset by 90° with respect to each other. The rows of teeth 9 each exhibit the same separation. Each of the rows of teeth 9 is offset by a quarter pitch with respect to each of the other rows of teeth 9, in order to improve the dosing precision.

The rear casing section 3 forms blocking elements 4 which engage with the rows of teeth 9. The piston rod 8 is blocked or locked by the engagement of the blocking elements 4, such that it is not possible to move the piston rod 8 counter to the advancing direction of the piston K. Movement of the piston rod 8 in the advancing direction, however, is permitted.

In order to advance the piston rod 8, the drive device (again, comprising the drive member 10 and operating element 18) engages with the rows of teeth 9 of the piston rod 8 via slaving means 11, behind the blocking elements 4. The operating element 18 is pushed from behind onto the drive member 10. The connection between the drive member 10 and the operating element 18 is such that the operating element 18 cannot be axially moved relative to the drive member 10, but can be rotated about the longitudinal axis L relative to the drive member 10. The longitudinal axis L forms a translational axis of the drive device and the driven device (consisting of the piston K and the piston rod 8), and also forms a rotational axis of the operating element 18.

The drive device viewed as a whole protrudes through the dosing member. The slaving means 11 of the drive member 10 can be bent free, in particular free from the dosing member, elastically outwards from the mesh, in the radial direction, in order to enable the drive device to move relative to the piston rod 8 counter to the advancing direction. The slaving means 11 are formed in a section of the drive device protruding forwards out of the dosing member; in the exemplary embodiment, they form the front end of the drive device. The engagement of the slaving means 11 and the shape of the rows of teeth 9 are such that the piston rod 8 is necessarily slaved by a movement of the drive device in a drive direction directed towards the piston K, said drive direction being identical to the advancing direction.

In the exemplary embodiment, the rows of teeth 9 are pointed in the advancing direction in the shape of serrated teeth. In modified embodiments, however, the piston rod 8 could comprise, instead of one or more rows of teeth 9, recesses or other engaging means for slaving means of a drive device, if it is only ensured that the piston rod 8 is necessarily slaved in the advancing direction but is prevented from being slaved counter to the advancing direction.

The dosing member is formed by a sleeve-shaped inner dosing body 13 and a sleeve-shaped outer dosing body 14, which are produced as separate parts and immovably connected to each other. In particular, it is not possible for the two dosing bodies 13 and 14 to either axially move or rotate about the longitudinal axis L relative to each other. The outer dosing body 14 concentrically surrounds the inner dosing body 13. A slight annular gap, into which the likewise sleeve-shaped rear casing section 3 protrudes, remains circumferentially between the two dosing bodies 13, 14.

The rear casing section 3, together with the dosing body, forms a swivel joint, more precisely a screw joint, which causes a rotational movement of the dosing member about the longitudinal axis L to result in a translational movement of the dosing member in or counter to the advancing direction, i.e., an axial translational movement relative to the rear casing section 3, depending on the direction of rotation. The longitudinal axis L forms a rotational axis and a translational axis of the dosing member. To form the swivel joint, the rear casing section 3 and the dosing member are in threaded engagement. The threaded engagement is between an inner thread 6 formed on an inner surface area of the rear casing section 3 and an outer thread 16 formed on an outer surface area of the inner dosing body 13. The threaded engagement could instead also be formed between an outer thread of the rear casing section 3 and an engaging inner thread of the outer dosing body 13. By rotating the dosing body, the user selects the product dosage to be administered. Since, through the threaded engagement, the dosing member also simultaneously performs an axial translational movement, a delivery stroke of the length Ah is set for the drive device, which corresponds to the product dosage selected.

The inner dosing body 13 forms a dosing stopper 15 which limits the movement of the drive device counter to the advancing direction. More precisely, a facing area of the inner dosing body 13 pointing in the advancing direction forms the dosing stopper 15 at its front end. The dosing stopper 15 is formed by an annular collar running around the longitudinal axis L, said collar protruding radially inwardly towards the drive member 10 via an inner surface area of the inner dosing body 13. The dosing stopper 15, more precisely its front stopper area, runs around the longitudinal axis L at an axially constant height, i.e., a linear dosing stopper 15 is formed at a single height.

Opposite the dosing stopper 15 in the advancing direction, the rear casing section 3 forms a delivery stopper 5 which limits the movement of the drive device in the advancing direction. The drive device can thus be moved in and counter to the advancing direction between the delivery stopper 5, which is fixed to the casing and even formed by the rear casing section 3 itself, and the translationally adjustable dosing stopper 15. The drive device in turn forms a counter stopper, namely the delivery and dosing stopper 12, on an outer surface area of the drive member 10. The delivery and dosing stopper 12 is formed by an annular collar via a front stopper area facing the delivery stopper 5 and a rear stopper area facing the dosing stopper 15. The delivery and dosing stopper 12 protrudes radially outwardly from an outer surface area of the drive member 10 towards a facing inner surface area of the rear casing section 3.

The rear casing section 3 is completely transparent or at least transparent in the section which overlaps a maximum delivery stroke of the drive device. The transparency serves to verify the axial position of the drive device, in particular the position of the drive member 10 which engages directly with the piston rod 8 and is rigidly connected to it via the engagement in the advancing direction.

For the purpose of a particularly precise optical verification, the drive member 10 is provided with a thin marking line, preferably a circumferential marking line, which is clearly visible through the rear casing section 3 and forms an indicator 32 (FIGS. 9 to 11). Advantageously, the delivery and dosing stopper 12 itself can form the marking line by forming a thin tip, radially outwardly. The delivery and dosing stopper 12 is suitable as an indicator for verifying, alone for the reason that it radially protrudes almost directly up to the rear casing section 3 or even contacts it in a sliding contact. A radially outer surface area of the delivery and dosing stopper 12 or the radially outer tip cited is preferably additionally provided with a thin marking line which is attached on the surface or in a recess on the surface or is formed in the material, and can advantageously be fluorescent.

As may be seen in connection with FIGS. 9 to 12, and in particular in FIG. 13, the rear casing section 3 comprises a dosage scale 30 over the length of a maximum delivery stroke Ahmax. The dosage scale 30 can be attached to the inner surface area or, in some embodiments, to the outer surface area of the rear casing section 3, or let into the transparent surface of the rear casing section 3. In the exemplary embodiment, it is attached to the outer surface area. The dosage scale 30 is formed by dosage numbers which indicate dosage units and by dosage marks 31. Each of the dosage numbers is assigned to one dosage mark 31. The dosage marks 31 are formed by short, thin lines which each extend in the circumferential direction of the rear casing section 3. The dosage numbers are arranged over the circumference of the casing section 3, ascending towards the rear, in the form of a spiral around the rotational axis L of the dosing member 13/14. Correspondingly, the dosage marks 31 are spirally arranged, such that each of the dosage marks 31 exhibits a different axial height to each of the other dosage marks 31. The dosage marks 31 thus represent, in a fine axial grading, every product dosage which can be selected and delivered, in whole dosage units. Due to the transparency of the rear casing section 3, the axial position of the drive device can be read, namely, as the axial position which the indicator 32 of the drive device assumes relative to the dosage marks 31. In the exemplary embodiment, the cited marking line running around the longitudinal axis L on the radially outer tip of the delivery and dosing stopper 12 forms the indicator 32 of the drive device.

In order to make it easier to read the dosage scale 30, in particular for people with low visual acuity, the outer dosing body 14 comprises a viewing window 34 in a surface section which overlaps the dosage scale 30, the viewing window being developed into a magnifier 34a. The viewing window 34 is sufficiently large and of such a shape that precisely one of the dosage numbers of the dosage scale 30 can be identified as the dosage selected, through the viewing window 34. In the exemplary embodiment, it is only ever possible to read exactly one dosage number through the viewing window.

In order that the dosage can be selected in discrete increments corresponding to the dosage numbers of the dosage scale 30, the dosing member and the rear casing section 3 are each in releasable latching engagement in discrete rotational angular positions which the dosing member can assume relative to the rear casing section 3. The latching engagement is formed between axially extending grooves 7 and engaging members 17 which engage with the grooves 7. In the exemplary embodiment, the axial grooves 7 are let into the rear casing section 3 on the outer surface area. The engaging members 17 are correspondingly formed as short latching cams on the inner facing surface area of the outer dosing body 14. The engaging members 17 are linearly guided axially in the axial grooves 7 in each of the discrete rotational angular positions of the dosing member.

A rear end position of the dosing member is defined by the engaging members 17 abutting a rear facing limiting area of the axial grooves 7. A front end position of the dosing member is defined by a rear connecting stay, which the dosing bodies 13 and 14 form between themselves, abutting against a rear facing area of the rear casing section 3. The dosing member (again, formed by bodies 13, 14) can be adjusted back and forth, from rotational angular latching position to rotational angular latching position, between these two extreme dosing positions, in order to axially adjust the dosing stopper 15. The maximum delivery stroke Ahmax of the drive device is as large as the axial distance which the dosing stopper 15 exhibits from the delivery stopper 5 in the rear end position of the dosing member minus the axial thickness of the delivery and dosing stopper 12.

Although the user can at any time freely alter the product dosage set between the two extreme dosing positions, it is advantageous for most applications if a dosage, once set, no longer has to be altered. The injection apparatus can therefore be flexibly set to the needs of different users on the one hand, and used with an optimal setting for a particular user for repeatedly administering the same product dosage. In this sense, a dosage memory is also simultaneously obtained through the dosing member which can be rotationally and translationally moved and therefore adjusted in combination relative to the rear casing section 3.

One advantage which should be recognized is that the dimensional accuracy and simple regulation of the dimensional accuracy and the stable design of the components which are used for dosing and delivery are realised using very few components. This contributes to the apparatus in accordance with the present invention having a simple design and being inexpensive, but nonetheless operating with precision and ensuring exact dosing.

The nested arrangement of the dosing bodies 13 and 14 is also advantageous, providing multi-functionality of the dosing member despite its simple construction. Thus, the dosing member directly forms the dosing engagement with the casing of the injection apparatus, the dosing stopper 15 for the drive device, a gripping part for the user and a part of a duplex dosage display, namely, the display for the dosage selected on the one hand and the display for the dosage which can be delivered on the other.

As a further advantage, the injection apparatus enables simple and reliable priming, i.e., bleeding the product-guiding parts between the piston K and the exit opening of the injection needle N.

Figure 3:
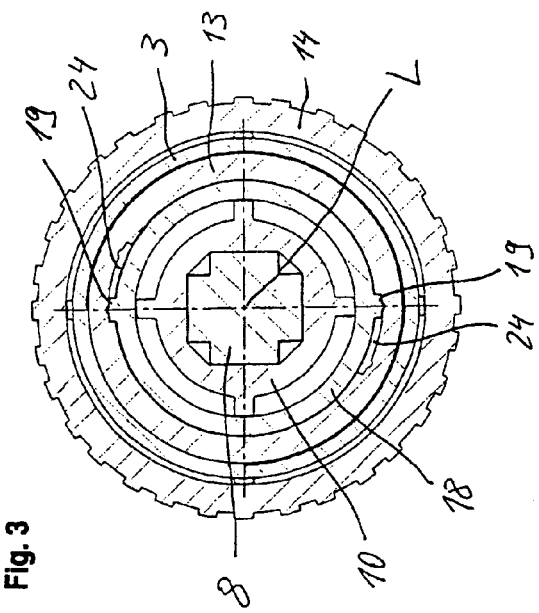
FIG. 3 depicts the injection apparatus in a cross-section.
Figure 5:
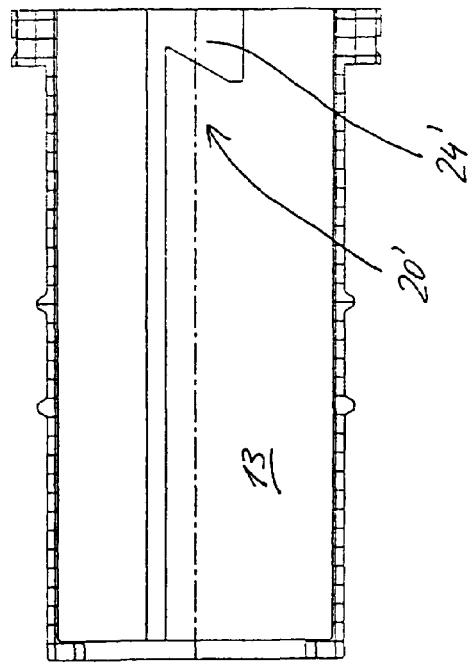
FIG. 5 depicts a modified dosing member in a longitudinal section.
Figure 4:
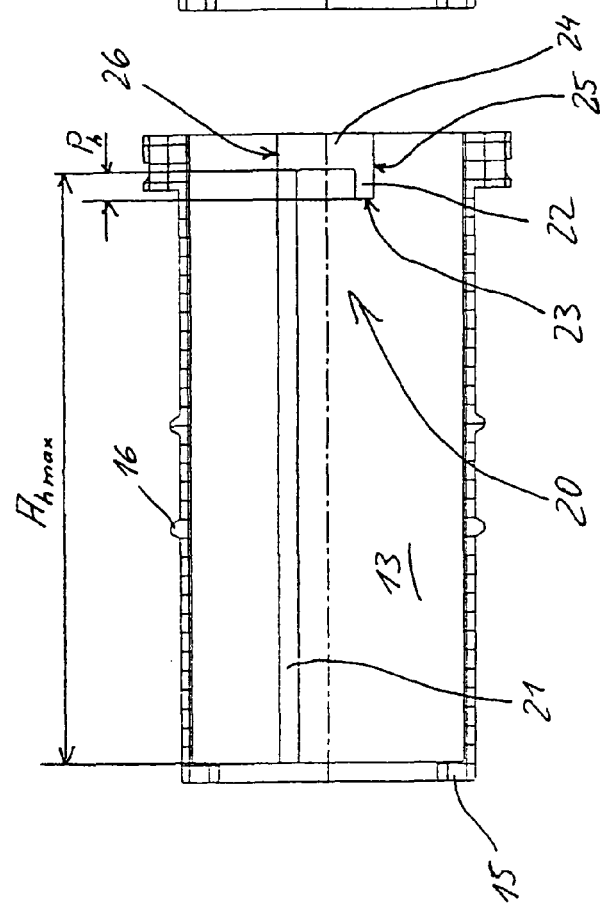
FIG. 4 depicts a dosing member of the injection apparatus in a longitudinal section.

To illustrate the priming function, reference is made to FIGS. 1 and 2 and in particular also to FIGS. 3, 4 and 5. In order to fulfil the priming function, the inner dosing body 13 and the operating element 18 are engaged. The engagement is between a guiding curve and an engaging member which engages with the guiding curve. The engaging member can be moved in a defined manner in the guiding curve between axial stoppers on the one hand and radial stoppers on the other. The guiding curve on the one hand and the engaging member on the other are formed on the mutually facing surface areas of the inner dosing body 13 and the operating element 18.

As shown in FIGS. 3 and 4, the engaging member indicated as 19 is formed on an outer surface area of the operating element 18, while the guiding curve indicated as 20 is let into the facing inner surface area of the inner dosing body 13. The guiding curve 20 comprises a long axial section, a delivery groove, 21 and a contrastively short axial section, a priming groove, 22 and a connecting section 24 which extends in the circumferential direction and connects the two axial sections 21, the delivery groove, and 22, the priming groove to each other, at their rear ends. The axial sections or guiding sections comprise grooves 21 and 22. The grooves may be referred to collectively as guiding grooves or either of the depicted grooves may be referred to as first and second guiding section. The two side walls of the axial sections 21, the delivery groove, and 22, the priming groove, which oppose each other in the circumferential direction in the area of the connecting section 24, form rotational stoppers 25 and 26 for the engaging member 19. Engaging member 19 moves in the axial section 22, the priming groove, and moves transversely to the axial section 21, the delivery groove. The long axial section, the delivery groove 21 extends in the advancing direction as far as or to the dosing stopper 15, more precisely up to the rear facing area of the annular collar forming the dosing stopper 15. The shorter axial section, the priming groove, 22 runs parallel to the axial section 21 and is formed as a short blind groove. A front facing area of the axial section, the priming groove, 22 forms a priming stopper 23. The axial sections 21, the delivery groove and 22, the priming groove, feed onto the rear facing end of the inner dosing body 13. The connecting section 24 is correspondingly open at the rear facing end. The engaging member 19 is formed by an axial rib formed on the outer surface of the operating element 18. This axial rib forms the priming counter stopper on its free front facing area.

Because the engaging member 19 engages with the guiding curve 20 formed in this way, the operating element 18 can perform the shape of the movement corresponding to the guiding curve 20, relative to the inner dosing body 13, namely any selected delivery stroke Ah up to the maximum delivery stroke Ahmax, the contrastively smaller priming stroke Ph and the rotational selecting movement. Since the operating element 18 is connected to the drive member 10 such that it cannot move axially but can rotate about the longitudinal axis L, the operating element 18 can be rotated back and forth between the two rotational stoppers 25, 26 without acting on the drive member 10. Axial translational movement in either the long axial section, the delivery groove, 21 or the short axial section, the priming groove, 22 is then only possible, however, together with the drive member 10.

Because the connecting section 24 is arranged on the rear ends of the axial sections 21, the delivery groove, and 22, the priming groove, the rotational movement of the operating element 18 between the two rotational stoppers 25 and 26, i.e., from the delivery position to the priming position and vice versa, is only possible when the drive member 10 is abutting the dosing stopper 15 via its delivery and dosing stopper 12. In this "loaded" position, the engaging member 19 can be moved by rotating the operating element 18 relative to the inner dosing body 13 against the rotational stopper 25 and thus into axial flush with the priming stopper 23. In this rotational angular position of the operating element 18, the priming position, the drive device can be moved in the advancing direction by axially pressing onto the operating element 18 up to the priming stopper 23. The axial length Ph of this priming stroke is only a few dosing units, for example two, three or four dosing units. The axial distance between the priming stopper 23 and the priming counter stopper formed by the engaging member 19 is correspondingly short.

It is advantageous if the operating element 18 is in releasable latching engagement with the inner dosing body 13, flush with the axial sections 21, the delivery groove, and 22, the priming groove, i.e., on the rotational stoppers 25, 26, respectively. In order to obtain the latching engagement with the inner dosing body 13 in each of the delivery position and the priming position, the engaging member 19 is again provided with a thin, axial latching cam on its narrow outer surface area, said cam coming to rest in the two rotational stopper positions of the operating element 18 in each of two axial latching grooves, the delivery groove 21, and the priming groove 22, formed correspondingly in the guiding curve 20.

In the exemplary embodiment, two identical guiding curves 20 and engaging members 19 are provided which diametrically oppose each other. In the variant in FIG. 4, the connecting section 24 runs, simply linearly, at a single axial height.

FIG. 5 shows a guiding curve 20 with a connecting section 24' whose front guiding wall leads from the priming stopper 23 obliquely backwards into the long axial section, the delivery groove, 21. Due to the oblique trajectory of the connecting section 24', a translational movement of the operating element 18—and of the drive member 10 together with it—counter to the advancing direction and relative to the piston rod 8 is caused by a reverse rotational movement of the operating element 18 from the rotational stopper 25 towards the rotational stopper 26. In accordance with the embodiment of a priming process, the user therefore does not have to specially retract the drive device again relative to the piston rod 8, i.e., load it. Rather, the winding or loading movement is forced by the reverse rotational movement. The guiding curve 20 in FIG. 5 otherwise corresponds to the guiding curve 20 in FIG. 4.

The functionality or operation and method of use of the injection apparatus will now be described.

Figure 6:
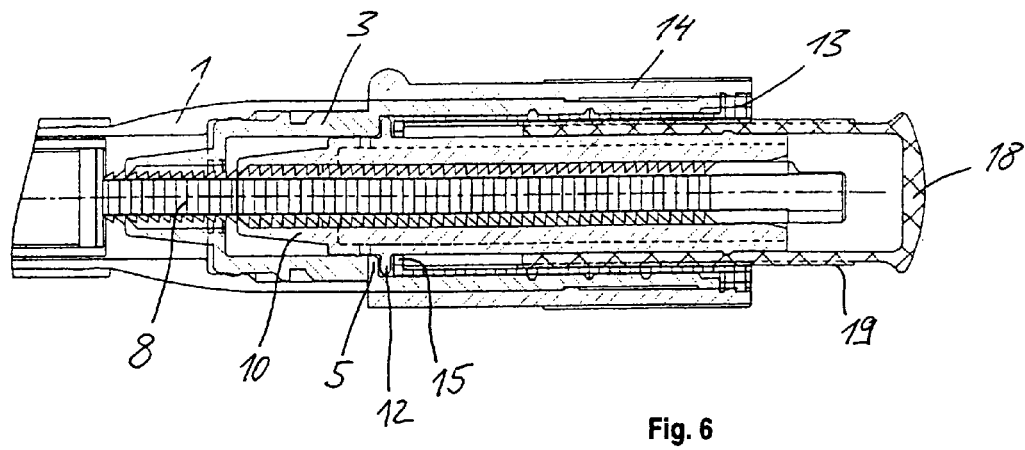
FIG. 6 depicts the rear part of the injection apparatus in a minimum-dosage state and "not loaded"

FIGS. 6 and 9 show the rear part of the injection apparatus in a longitudinal section, and each in a view in a state from which the dosage can be selected. Correspondingly, the drive device (comprising drive member 10 and operating element 18) abuts the delivery stopper 5, and the dosing member (comprising dosing bodies 13, 14) assumes its axially front end position. A slight distance remains between the delivery and dosing stopper 12 of the drive device and the dosing stopper 15 of the dosing member, the distance corresponding to two dosing units. Accordingly, the dosage of two dosage units can be read in the viewing window 34. Furthermore, the dosage mark 31 assigned to this dosage can also clearly be seen. Since the drive device abuts the delivery stopper 5 via its delivery and dosing stopper 12, the marking line of the drive device forming the indicator 32 runs parallel to the dosage mark 31, with an axial distance. The distance corresponds to two dosage units. This situation can be seen in FIG. 9. The injection apparatus is "loaded" by retracting the drive device, relative to the piston rod 8, up to the dosing stopper 15. When this loading movement has been performed, two dosing units can be delivered by then advancing the drive device and the thereby slaved or driven piston rod 8. FIG. 10 shows this state, in which the drive device abuts the dosing stopper 15 of the dosing member via its delivery and dosing stopper 12. The dosing mark 31 assigned to the dosage number "2" and the indicator 32 overlap each other exactly.

From the state shown in FIGS. 6 and 9, the user selects the dosage. To select the dosage, the dosing member has merely to be rotated about the longitudinal axis L relative to the rear casing section 3. Here, the outer dosing body 14 forms a gripping part and the inner dosing body 13 forms a dosing screw whose rotational movement is directly converted into the axial adjusting movement by the threaded engagement, for the purpose of selecting the dosage. Dosing is in discrete rotational angular latching positions which the dosing member successively assumes relative to the rear casing section 3.

Figure 7:
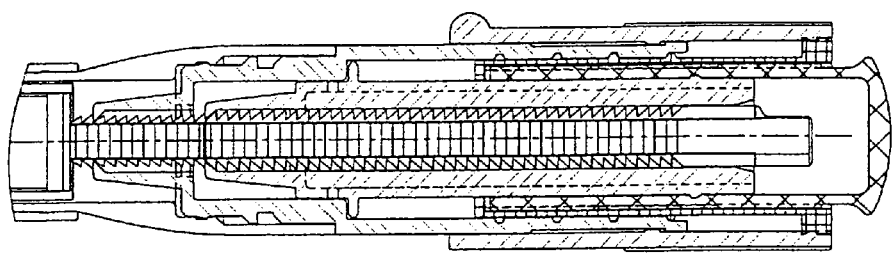
FIG. 7 depicts the rear part of the injection apparatus in a maximum-dosage state and "not loaded"

FIGS. 7 and 11 show the injection apparatus directly after the dosage has been selected. A dosage of 42 dosage units has been set, as can be read in the viewing window 34 in FIG. 11. In the state shown in FIG. 7, selecting the dosage has been concluded but the injection apparatus is not yet "loaded", for the drive device is still abutting the dosing stopper 5. This is indicated on the dosage scale 30 by the indicator 32, as can be seen in FIG. 11.

Figure 8:
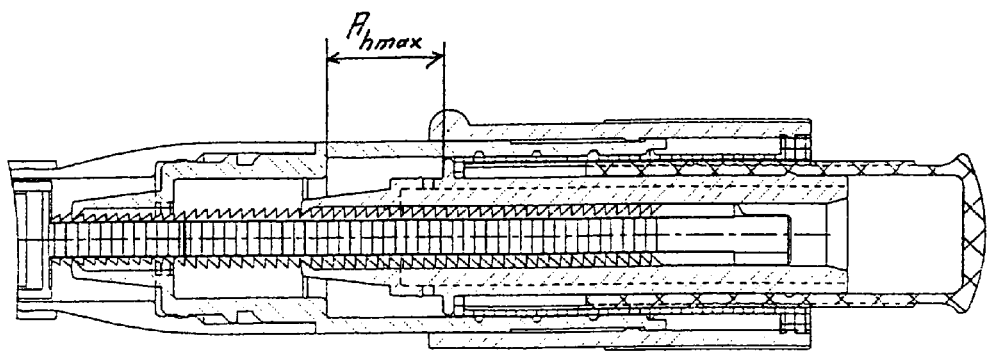
FIG. 8 depicts the rear part of the injection apparatus in the maximum-dosage state and "loaded"

FIG. 8 shows maximum dosing. FIG. 12 shows the injection apparatus in a state in which selecting the dosage has been concluded but the drive device has not been retracted by the thus defined delivery stroke of length Ah, but rather only by a part of this stroke. In the state shown by way of example in FIG. 12, the drive device has been retracted by a stroke corresponding to a product dosage of eight dosage units. This is indicated in FIG. 12 by the axial position of the indicator 32 on the dosage scale 30.

As illustrated in FIG. 12, a simple but reliable display of the remaining amount is obtained through the transparency of the rear casing section 3, the form of the indicator 32 and the arrangement of the dosage scale 30. For if the ampoule 2 no longer contains the full selected product dosage of for example 42 dosage units before the drive device 10/18 is retracted, then the drive device can only be retracted counter to the advancing direction until the length of its next delivery stroke in the advancing direction corresponds to the product dosage still available in the ampoule 2 for a final delivery. In the example embodiment, this remaining amount is eight dosage units. The indicator 32 and the dosage mark 31 assigned to the dosage of eight dosage units correspondingly overlap each other. The remaining amount which can be delivered is defined by a stopper acting between the piston rod 8 and the drive device. This stopper limits the effective length of the piston rod 8, i.e., the length by which the piston rod 8 can be moved as a whole in the advancing direction, from its position before a first delivery up until the ampoule 2 has been emptied. In the exemplary embodiment, the piston rod 8 forms this stopper for the slaving means 11 in its rear part, i.e., the slaving means 11 cannot elastically evade this stopper.

In the foregoing description, embodiments of the present invention, including preferred embodiments, have been presented for the purpose of illustration and description. They are not intended to be exhaustive or to limit the invention to the precise forms and steps disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An administering apparatus for administering a fluid product, comprising:
    a) a casing comprising a reservoir for the product;
    b) a driven device which acts on the product contained in the reservoir, in order to deliver the product; and
    c) a drive device which acts on the driven device and performs a delivery stroke in a drive direction from a delivery position up to a delivery stopper, in order to deliver a product dosage to be administered; wherein
    d) a priming stopper is provided for the drive device and limits a priming stroke of the drive device, which serves to bleed, in the drive direction, wherein the priming stroke is axially shorter than a maximum delivery stroke, and wherein the drive device can be moved in the drive direction from a priming position to the priming stopper, and transversely to the drive direction in the delivery position, and the drive device is moveable from the delivery position to the priming position;
    e) a dosing member comprising two dosing bodies nested and connected to each other, one of which forms a sleeve-shaped, cylindrical outer dosing body and the other of which forms a sleeve-shaped, cyclindrical inner dosing body, wherein the outer dosing body concentrically surrounds the inner dosing body, between which a circumferential gap remains, into which the casing protrudes, and wherein a guiding curve is formed on a surface of the inner dosing body; and
    f) an engaging member formed by the drive device, which serves as a priming counter stopper and engages with the guiding curve forming the priming stopper, wherein the guiding curve comprises a first guiding section, a second guiding section parallel to the first guiding section and a connecting section which extends in the circumferential direction to connect a rear end of the first guiding section and a rear end of the second guiding section to each other.

2. The administering apparatus as set forth in claim 1, the inner dosing body further comprising another stopper which defines the delivery position and limits the movement of the drive device from the priming position to the delivery position.

3. The administering apparatus as set forth in claim 2, wherein the inner dosing body further comprises a third stopper, which defines the priming position and limits rotational movement of the drive device to the priming position.

4. The administering apparatus as set forth in claim 3, wherein the movement of the drive device from the priming position to the delivery position is a rotational movement about a rotational axis pointing in the drive direction.

5. The administering apparatus as set forth in claim 1, wherein the inner dosing body forms a dosing stopper for the drive device, and wherein the dosing member is moveably coupled to the casing by a swivel joint for axially adjusting the dosing stopper in or counter to the drive direction.

6. The administering apparatus as set forth in claim 1, wherein the guiding curve and the priming counter stopper are formed on mutually facing surface areas.

7. The administering apparatus as set forth in claim 6, wherein the drive device and the casing are engaged via the guiding curve and the priming counter stopper to define the priming stroke.

8. The administering apparatus as set forth in claim 1, wherein the engaging member can only engage with one of the guiding sections at a time and can be moved from one guiding section to the other via the connecting section of the guiding curve.

9. The administering apparatus as set forth in claim 1, wherein the inner dosing body of the dosing member forms a dosing stopper and performs a dosing movement relative to the casing, which adjusts a distance between the delivery stopper and the dosing stopper which, measured in the drive direction, defines the length of the delivery stroke.

10. The administering apparatus as set forth in claim 9, wherein the drive device can be moved counter to the drive direction up to the dosing stopper.

11. The administering apparatus as set forth in claim 9, wherein the dosing movement of the dosing member comprises a translational movement in or counter to the drive direction.

12. The administering apparatus as set forth in claim 11, wherein the dosing movement of the dosing member is a combination of a translational movement in or counter to the drive direction and a rotational movement about a rotational axis pointing in the drive direction.

13. The administering apparatus as set forth in claim 1, wherein one of the dosing bodies is in threaded engagement with the casing about a rotational axis extending in the drive direction, and the other is at least translationally slaved by a rotational movement about the rotational axis.

14. The administering apparatus as set forth in claim 13, wherein the drive device comprises a drive member and an operating element which are connected to each other such that they are secured against shifting in and counter to the drive direction and can rotate relative to each other about a rotational axis pointing in the drive direction, wherein the drive member engages with the driven device in order to slave the driven device when the drive device moves in the drive direction, and the operating element serves to operate the drive device.

15. The administering apparatus as set forth in claim 14, wherein the operating element forms a priming counter stopper for the priming stopper.

16. The administering apparatus as set forth in claim 15, wherein the driven device comprises a piston which can be moved in the reservoir towards an outlet of the reservoir to deliver product, and a piston rod which engages with the drive device, the piston rod comprising at least one row of teeth extending axially, and the drive device comprising slaving means engaging the at least one row of teeth whereby the drive device slaves the driven device in the drive direction.

17. The administering apparatus as set forth in claim 1, wherein the administering apparatus is an injection apparatus comprising an injection cannula of at most 30 gauge, preferably 31 or 32 gauge, or an injection cannula having an outer diameter of at most 320 µm and an inner diameter not specified in ISO 9626, wherein the wall thickness is thinner than is specified in ISO 9626.

18. The administering apparatus according to claim 1, wherein the priming stroke is at least twenty times shorter than the maximum delivery stroke.

19. An administering apparatus for administering a fluid product, comprising:
 a) a casing comprising a reservoir for the product;
 b) a driven device which acts on the product contained in the reservoir to administer the product;
 c) a drive device which acts on the driven device and performs a delivery stroke in a drive direction from a delivery position to a delivery stopper to deliver a product dosage to be administered;
 d) a dosing member, comprising a dosing stopper, for performing a dosing movement relative to the casing and adjusting a distance between the delivery stopper and the dosing stopper thereby defining the length of the delivery stroke, wherein the dosing member comprises two dosing bodies immovably connected to each other, one of which forms a cylindrical, sleeve-shaped inner dosing body and the other of which forms a cylindrical, sleeve-shaped outer dosing body, between which a gap remains into which the casing protrudes, wherein the inner dosing body forms the dosing stopper;
 e) a priming stopper for the drive device to limit a priming stroke, the priming stopper comprising a guiding curve formed on a surface of the inner dosing body, wherein the guiding curve comprises a first guiding section, a second guiding section parallel to the first guiding section and a connecting section which extends generally circumferentially and connects a rear end of the first guiding section and a rear end of the second guiding section, and wherein the connecting section comprises a front guiding wall which leads from the priming stopper obliquely to the second guiding section;
 f) a priming counter stopper comprising an engaging member, said engaging member formed by a portion of an operating element of the drive device; and
 g) the priming stroke defined at least in part by the priming stopper that limits a movement of the priming counter stopper in the drive direction, wherein the priming stroke is axially shorter than a maximum delivery stroke, and wherein the drive device is moveable in the drive direction from a priming position to the priming stopper, and transversely to the drive direction in the delivery position, and the drive device is moveable from the delivery position to the priming position.

20. The administering apparatus according to claim 19, wherein the reservoir for the product is a disposable module.

21. The administering apparatus as set forth in claim 19, wherein the movement of the drive device from the priming position to the delivery position is a rotational movement about a rotational axis extending along the drive direction.

22. The administering apparatus as set forth in claim 19, wherein the inner dosing body which forms the dosing stopper for the drive device is moveably coupled to the casing by a swivel joint for axially adjusting the dosing stopper in or counter to the drive direction.

23. The administering apparatus as set forth in claim 19, wherein the guiding curve and the priming counter stopper are formed on mutually facing surface areas.

24. The administering apparatus as set forth in claim 19, wherein the drive device and the casing are engaged via the guiding curve and the priming counter stopper to define the priming stroke.

25. The administrating apparatus as set forth in claim 19, wherein one of the first guiding section and the second guiding section is a delivery guiding section comprising a delivery groove and the other guiding section is a priming guiding section comprising a priming groove, wherein the delivery groove is longer than the priming groove.

26. The administering apparatus as set forth in claim 19, wherein the engaging member can only engage with one of the guiding sections at a time and can be moved from one guiding section to the other via the connecting section of the guiding curve.

27. The administering apparatus as set forth in claim 19, wherein the drive device comprises a drive member and the operating element connected to each other such that they are secured against shifting in and counter to the drive direction and can rotate relative to each other about a rotational axis extending in the drive direction, wherein the drive member engages with the driven device to slave the driven device when the drive device moves in the drive direction, and wherein the operating element serves to operate the drive device.

28. The administering apparatus as set forth in claim 27, wherein the drive device can be moved counter to the drive direction up to the dosing stopper.

29. The administering apparatus as set forth in claim 28, wherein the dosing movement of the dosing member comprises a translational movement in or counter to the drive direction.

30. The administering apparatus as set forth in claim 29, wherein the dosing movement of the dosing member is a combination of a translational movement in or counter to the drive direction and a rotational movement about a rotational axis extending in the drive direction.

31. The administering apparatus as set forth in claim 30, wherein one of the dosing bodies is in threaded engagement with the casing about a rotational axis pointing in the drive direction, and the other is at least translationally slaved by a rotational movement about the rotational axis.

32. The administering apparatus as set forth in claim 31, wherein the driven device comprises a piston which can be moved in the reservoir towards an outlet of the reservoir, to deliver product, and a piston rod which engages with the drive device.

33. The administering apparatus as set forth in claim 32, wherein the piston rod comprises at least one row of teeth extending axially, and the drive device comprises at least one slaving means which engages with the at least one row of teeth, so that the drive device slaves the driven device in the drive direction.

34. The administering apparatus as set forth in claim 33, wherein the administering apparatus is an injection apparatus comprising an injection cannula of at most 30 gauge, preferably 31 or 32 gauge, or an injection cannula having an outer diameter of at most 320 μm and an inner diameter not specified in ISO 9626, wherein the wall thickness is thinner than is specified in ISO 9626.

35. The administrating apparatus as set forth in claim 1, wherein one of the first guiding section and the second guiding section is a delivery guiding section comprising a delivery groove and the other guiding section is a priming guiding section comprising a priming groove, wherein the delivery groove is longer than the priming groove.

* * * * *